United States Patent [19]
Stephen

[11] Patent Number: 5,344,440
[45] Date of Patent: Sep. 6, 1994

[54] METHOD AND APPARATUS FOR STIMULATING GROWTH AND HEALING OF LIVING TISSUES

[76] Inventor: Richard L. Stephen, 3717 Wild Bird Cir., Dayton, Ohio 45430

[21] Appl. No.: 974,098

[22] Filed: Nov. 10, 1992

Related U.S. Application Data

[63] Continuation-in-part of Ser. No. 616,543, Nov. 21, 1990, abandoned.

[51] Int. Cl.⁵ ............... A61N 1/04; A61N 1/18
[52] U.S. Cl. ............... 607/139; 607/148; 607/149; 607/152; 607/153
[58] Field of Search ........ 607/115, 135-141, 607/148, 149, 152, 153; 128/644

[56] References Cited

U.S. PATENT DOCUMENTS

| | | | |
|---|---|---|---|
| 3,279,468 | 10/1966 | Le Vine | 607/140 |
| 3,376,870 | 4/1968 | Yamamoto et al. | 607/141 |
| 3,490,439 | 1/1970 | Rolston | 128/644 |
| 3,508,541 | 4/1970 | Westbrook et al. | 128/644 |
| 3,612,061 | 10/1971 | Collins et al. | 607/148 |
| 3,669,119 | 6/1972 | Symmes | 607/141 |
| 3,848,608 | 11/1974 | Leonard | 607/148 |
| 4,535,779 | 8/1985 | Ober | 607/153 |
| 4,583,547 | 4/1986 | Granek et al. | 128/644 |
| 4,751,928 | 6/1988 | Hallon et al. | 128/644 |

FOREIGN PATENT DOCUMENTS

| | | | |
|---|---|---|---|
| 988247 | 4/1965 | United Kingdom | 607/139 |
| 2160427 | 12/1985 | United Kingdom | 607/139 |

Primary Examiner—Lee S. Cohen
Attorney, Agent, or Firm—Ralph H. Dougherty

[57] ABSTRACT

An improved method and apparatus for stimulating the growth and healing of living, especially human, tissues, promoting the healing of wounds and skeletal fractures. An electrical apparatus consists of a baseplate, made of lightweight nonconductive material, for encompassing all or a portion of a body member. A multiplicity of generally evenly spaced holes are provided in the baseplate and a probe adapter including a moveable electrically conductive probe is situated within the holes, as desired. An electric contact connects the interior of each adapter and the probe situated therein to a terminal on the baseplate. Each probe is individually adjustable to contact the wearer's body part within the base member regardless configuration of the body part, thus allowing treatment of all or a selected portion of the body part.

16 Claims, 3 Drawing Sheets

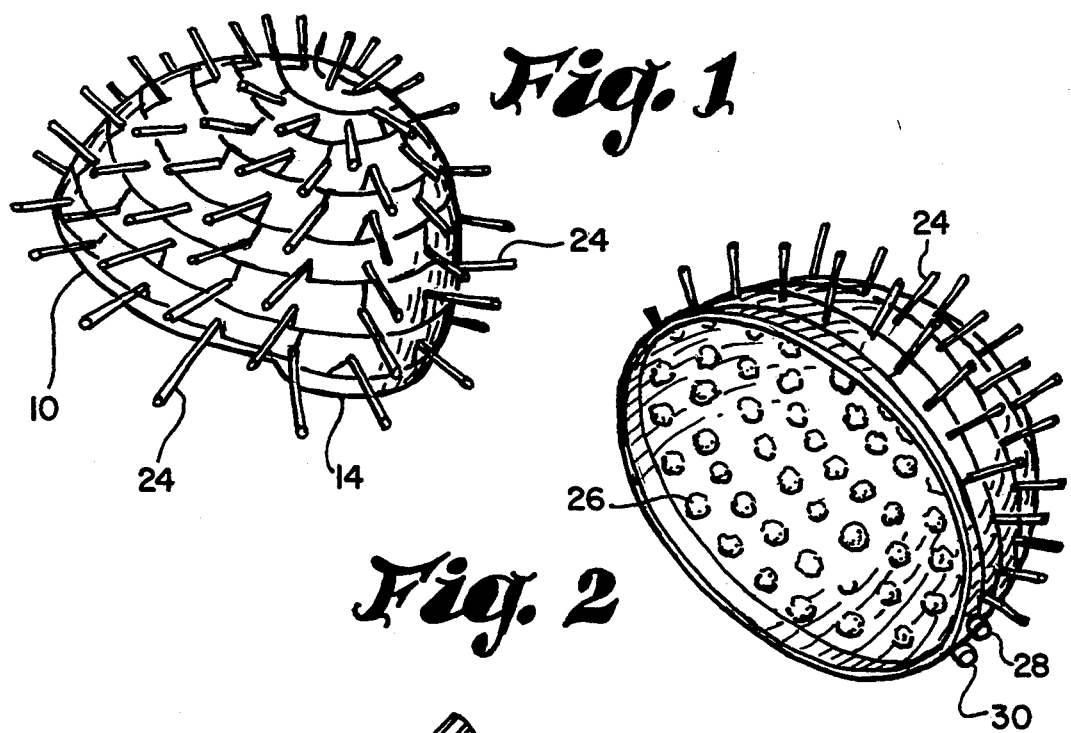
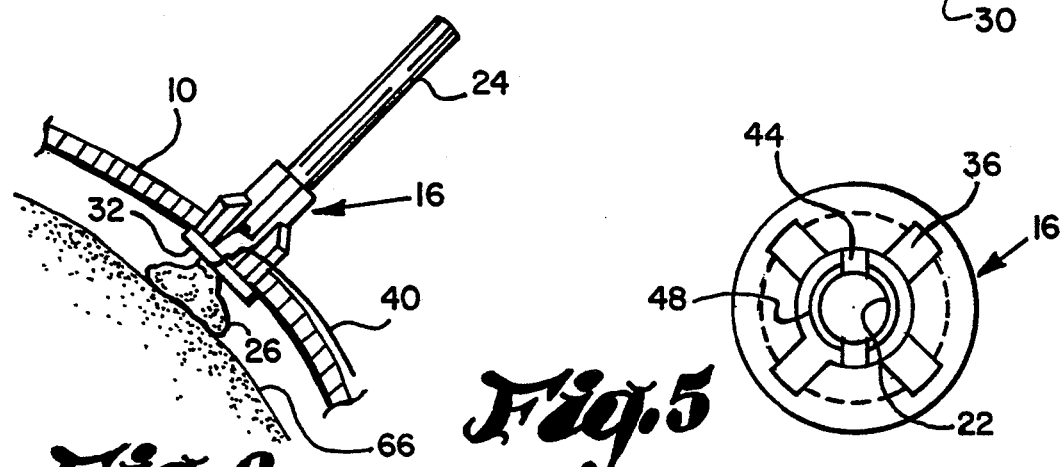
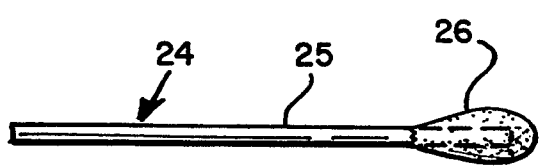
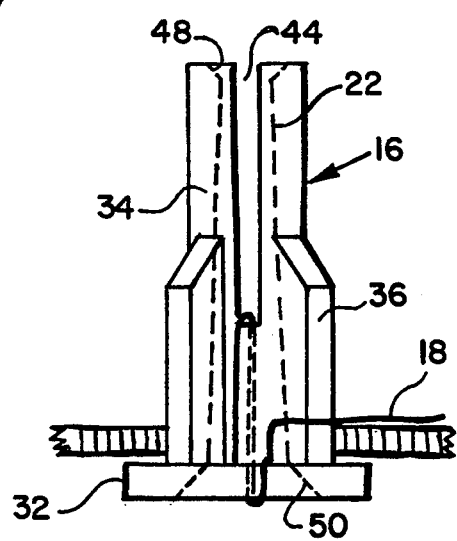

METHOD AND APPARATUS FOR STIMULATING GROWTH AND HEALING OF LIVING TISSUES

CROSS REFERENCE TO RELATED APPLICATION

This application is a continuation-in-part application of my co-pending U.S. patent application Ser. No. 07/616,543, filed Nov. 21, 1990, now abandoned.

FIELD OF THE INVENTION

The present invention relates to a method and apparatus for stimulating the growth and healing of living mammalian, especially human, tissues, promoting the healing of wounds and skeletal fractures, and more particularly to electrical apparatus and methods for stimulating the scalp of a human being. The invention is applicable to both cosmetic and medical treatment of tissue.

BACKGROUND OF THE INVENTION

It has been shown that such exogenous electrical stimulation will stimulate growth of skeletal tissue in non-united fractures, as well as speeding healing in soft tissue wounds (see Becker and Selden, The Body Electric Electromagnetism; New York; Quill; 1985; pages 163-180). These researchers demonstrated that electrical current directly stimulates cell dedifferentiation of red cells and that these then redifferentiated as cartilage, which continue on to become bone cells.

Pulsed electrical stimulation has been found to promote the healing of wounds with high current densities and without tissue irritation or burning. Types of wounds responsive to electrical stimulation include burn wounds, lacerations and abrasions. Electrical stimulation accelerates the healing process, and it is believed to also reduce the incidence of infection, decrease scarring, reduce trauma from injury, as well as trauma following surgery. It is especially useful in healing of skin grafts. Electrical stimulation can relieve muscle spasms, help activate atrophied muscles, and assist in reeducation of spastic muscles.

Electrical stimulation has the potential of decreasing headache pain, and other head pain, regardless of the source of pain, such as improper blood circulation, neuromuscular problems or a combination thereof. It can also promote mental relaxation, in a manner similar to biofeedback treatments.

In 1983, Dr. William Bauer, of the Veterans Administration Medical Center in Cleveland, Ohio, reported success with head and neck pain by treatment with transcutaneous electrical nerve stimulation (TENS).

Electrical stimulation of the epidermis can reduce the incidence of dry scalp, psoriasis, and dandruff. It has also been used to treat ulcers and skin infections.

Masaki U.S. Pat. No. 4,841,972, entitled LOW-FREQUENCY TREATMENT DEVICE DIRECTED TO USE IN BATH, teaches a low frequency treatment for use in a bath, such as a bathtub, including means for oscillating a surged treatment wave and vibrating means for massaging the epidermis.

Masaki British Patent Publication GB 2160426A, entitled ELECTROTHERAPEUTIC APPARATUS, teaches an electrotherapeutic apparatus including a low frequency generator which is worn on the head as a part of the apparatus, and has a frontal electrode for engaging the user's brow, and an upper central electrode for engaging the top of the user's scalp, both electrodes being provided with an absorbent material cover, such as sponge.

The patents which employ one or more vibration units create so much weight, which are so heavy on the head of a user, that continued use is unlikely. I have invented an apparatus which avoids the heavy weight of such units, and requires neither vibrational massage nor medication to effectively promote growth and healing of living tissue. The invented device may be used in conjunction with existing neuro-stimulation and muscle stimulation devices, as well as DC electrical skin care units operated by batteries.

SUMMARY OF THE INVENTION

The invented apparatus consists of a baseplate, such as a headpiece, for encompassing all or a portion of a body member, such as a scalp. The baseplate preferably is made of plastic or other lightweight non-conductive material. A multiplicity of generally evenly spaced holes are provided in the baseplate and each hole receives a probe adapter having a hole therethrough. A probe having an electrically conductive outer skin is provided within each of the probe adapters. An electric wire or electric contact connects the interior of each adapter to a terminal on the baseplate. Each probe is individually adjustable to contact the wearer's body part within the base member regardless of the configuration of the body part. Thus, by causing the probe to make contact or removing the probe from contact with the wearer's body, treatment of an entire body part, such as a scalp, or only a small area can be effected.

The present invention is useful for cosmetic purposes and for medical purposes, including promoting healing and growth of both skeletal and soft tissues. Stimulation of human tissues by electrical means has been shown to be effective in promoting healing and in skin care.

OBJECTS OF THE INVENTION

The principal object of the present invention is to provide an improved device for promoting healing of both skeletal tissue and soft tissue of a mammal.

Another object of the invention is to provide electrical apparatus for promoting healing of human tissue without further injury or burning of tissue.

Another object of the invention is to provide apparatus for decreasing headache pain.

BRIEF DESCRIPTION OF THE DRAWINGS

The foregoing and other objects will become more readily apparent by referring to the following detailed description and the appended drawings in which:

FIG. 1 is an isometric view of the outside of one embodiment of the invented device for use on a human head.

FIG. 2 is an isometric view of the embodiment of FIG. 1 showing a portion of the interior.

FIG. 3 is a cross-sectional view of a portion of the oval-shaped headpiece of FIG. 1 taken through a probe and probe adapter, showing the probe contacting the scalp of a user.

FIG. 4 is a side view of a probe.

FIG. 5 is a top view of a probe adapter.

FIG. 6 is a side view of the probe adapter of FIG. 5.

DETAILED DESCRIPTION

Figure 7:
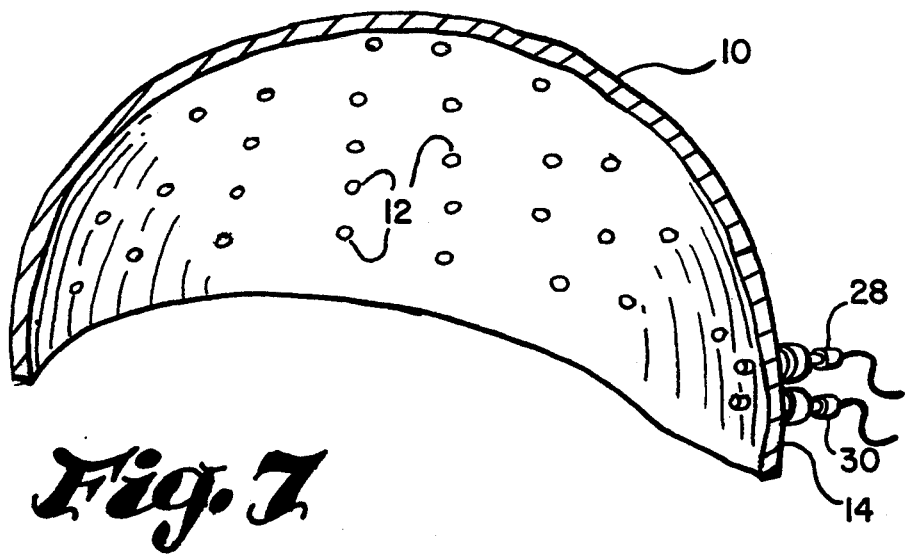
FIG. 7 is a cross-sectional view of the oval shaped base headpiece of FIG. 1.

Referring now to the drawings, and particularly to FIG. 1, the invented device includes a baseplate member, such as oval-shaped hood or headpiece 10 having a multiplicity of holes 12 therethrough at regularly spaced intervals, as shown in FIG. 7. Any number of holes 12 can be provided in the base plate, but preferably they should be about 2 to 3 centimeters apart and should cover substantially all of the base plate. The oval-shaped hood can have a downwardly extending portion 14 adapted to cover the rear of a head. Situated in each hole 12 is a removable probe adapter or electrode socket 16 having an electrical contact 18 communicating with its center and having a central elongated opening 22 within which the electrical contact is situated.

Positionable within the central elongated opening 22 of probe adapter 16 is a probe 24, having a shank 25, and preferably having a rounded end 26, and either being made of an electrically conductive material or having an electrically conductive skin. A pair of electric contacts 28, 30 are situated in the head piece for connection to a low voltage power source.

The probe adapter 16, as shown in FIGS. 3, 5 and 6, can be as simple as a plastic insert having a base 32, a central elongated portion 34 upstanding from the base 32 and tapered or partially tapered retaining flanges 36 for wedging into the hole 12. The probe adapter is inserted into the baseplate 10 from the interior, with the base 32 mating against the inside of the baseplate 10 as shown in FIGS. 3 and 6. A contact wire 40 passes down through the inside of the elongated hole 22 wherein it is situated for making contact with the probe 24. Alternatively, the interior of the central elongated opening 22 can be lined with an electrical contact or partially lined with a thin electrical contact embedded in the sidewall of the central elongated opening 22, or even a printed circuit on the sidewall.

The four flanges 36 or protrusions fill the hole diameter and create a gripping mechanism with the sides of hole 12. The elongated end of the probe adapter 16 which extends outwardly through the base plate opposite the base 32 preferably is provided with one or more elongated slots 44 (two are shown), and with a tapered interior of the central hole 22. The elongated slots in the adapter effect a spring action against side of the probe shank 25 when the probe is inserted into the probe adapter 16. Advantageously, a funnel-shaped bevel or chamfer 48 is provided at the upper end of the probe adapter for easy positioning of a probe into the adapter. Likewise, a similar funnel-shaped bevel or chamfer 50 is provided at the lower end of the probe adapter to facilitate withdrawal of a probe through the adapter.

Figure 8:
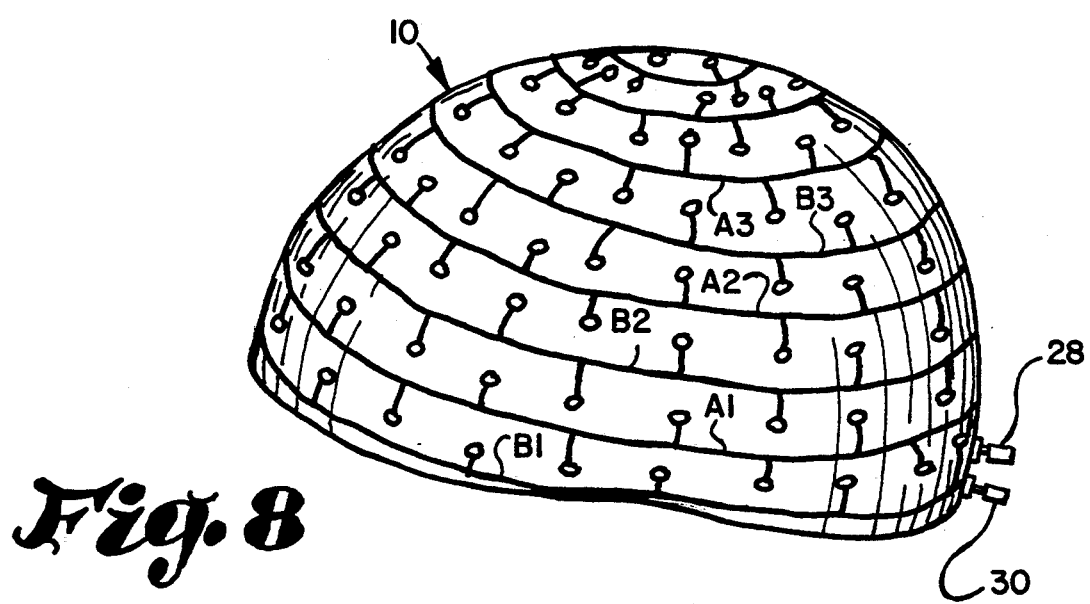
FIG. 8 is an isometric view of the exterior of the oval-shaped headpiece of FIGS. 1 and 7 showing the placement of the holes for accommodating the probe adapters.

The contact 28 communicates with approximately one half of the probe adapter holes 12 through circuits A, A1, A2, A3, etc., while contact 30 communicates with the remaining probe adapter holes 12 through circuits B, B1, B2,, B3, etc., as best shown in FIG. 8. Printed circuits can be provided in place of wires, and such printed circuits can be positioned on either the exterior or interior of the baseplate 10.

Figure 9:
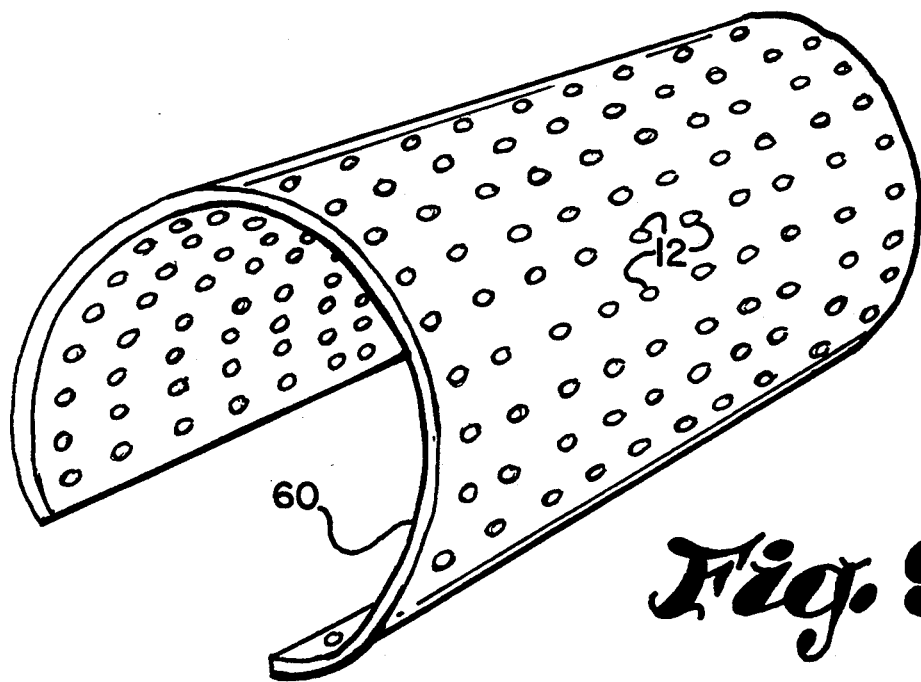
FIG. 9 is an isometric view of the exterior of an alternative elongated base member showing the placement of the holes for receiving probe adapters.
Figure 10:
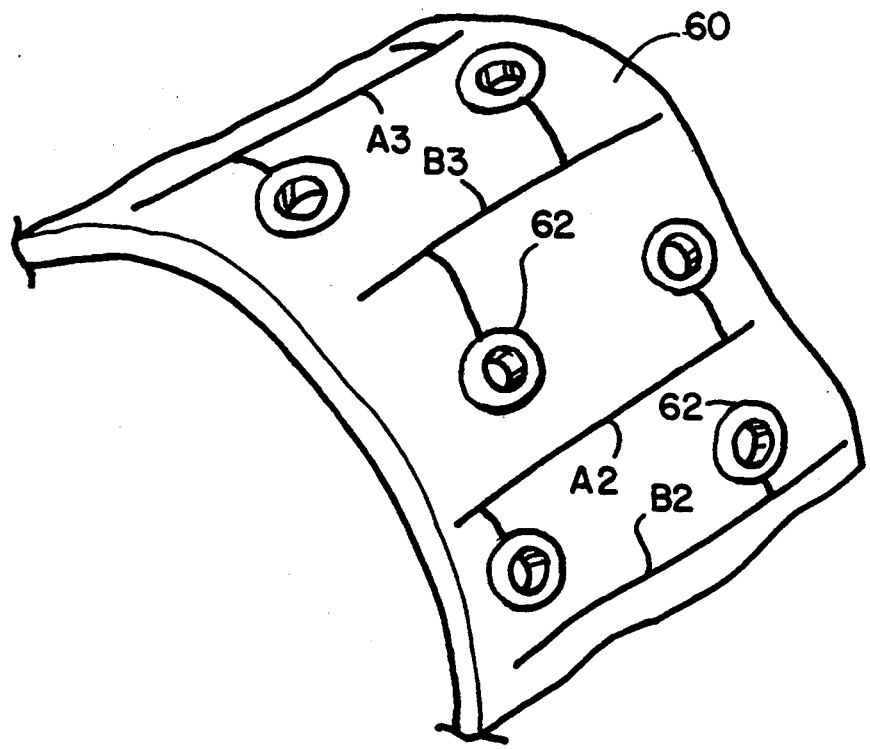
FIG. 10 is a partial isometric view of a portion of the exterior of the elongated base member of FIG. 9 showing alternative electrical connections.

The baseplate 60 shown in FIGS. 9 and 10 is preferably made of a flexible plastic, or other non-conductive material, so it can be spread to accommodate a limb of the user, or it could even be sufficiently large to encompass the torso of a user in special situations. FIG. 10 shows an alternative electrical contact 62 for receiving a probe 24, the contact 62 being made of a conductive material, containing a conductive material, or being at least partially covered and lined with a printed circuit.

In operation, probe adapters 16 are inserted into the adapter holes 12 from the inside of the baseplate 10, with the flange or base 32 of each adapter mated against the baseplate. Probes 24 are dampened with water to enhance conductivity, and are inserted shank first from the inside of the baseplate 10 into each elongated hole 44 in each adapter 16 to a depth sufficient that the end 26 will contact the subject's head 66 in those areas of the head to be treated. The oval-shaped hood is placed on the head of a human being for the purpose of electrical stimulation. Low voltage power is connected to the contacts 28, 30 and power is supplied to the apparatus, passing through the probe 24 and stimulating the scalp. Only small amounts of energy are transmitted, in the range of microamperes or milliamperes. There is no feeling of vibration or other discomfort to the wearer of the headpiece during treatment. The only feeling observed by the user is the light weight of the headpiece, which is distributed evenly by the many probes which contact the scalp, and the dampness of the probes from use of water to transmit the variations of current and waveform. Vibration, oscillation or other similar types of discomforting energy are avoided.

In treating the scalp, probes in alternating holes are connected to different electrical poles, i.e., having alternating positive and negative polarity. In other treatments, it may be desirable for all probes to have the same polarity, for instance to attract oxygen to the probe for the purpose of healing a wound.

It has been found that vibration, medication, or massage is unnecessary to achieve the desired result. The probes are soft tipped, and disposable, so the device is easy to clean, and to use on multiple patients. The probes are not invasive, so do not physically damage sensitive tissues. Because the entire apparatus is light in weight, the scalp treatment version usually weighing about 8 ounces, the device is portable, and can be carried conveniently for treatment anywhere.

The probes may be dampened with water either prior to insertion in the probe adapter, or after insertion but before placement in contact with the body part to be treated. Any convenient means of dampening the probes may be used, including spraying water directly on them, and immersing the probes in water.

The invented device can be utilized on a human head to reduce headache pain. In this case, the probes are brought into contact with the scalp selectively in the areas where such pain is noted by the user.

Although the foregoing discussion has related principally to scalp treatment, by utilizing a base member having a configuration shown in FIG. 9, a broken or burned limb can be treated in generally the same manner as described above. Probe adapters are inserted from the inside of the baseplate, and the baseplate is placed around the limb to be treated. Probes are inserted into the probe adapter from the interior of the device to a depth to make contact with the exterior of the limb, current flow is begun, and continued for a predetermined period, generally for from 5 to 15 minutes per treatment.

The invented method for stimulating the growth and healing of living tissues comprises at least partially encompassing a body part, such as an arm or even a torso, with a base member having a multiplicity of electrically conductive adjustable probes, each probe being adapted for selectively engaging the body part by the amount of protrusion of each probe being adjusted as appropriate to contact the desired body part; bringing the desired number of probes into engagement with the body part; then passing low voltage power through the probe, stimulating the growth or healing of tissue encompassed by the base member. The probe is preferably wetted with an electrolyte before contacting the body part, the preferred electrolyte being water in the form of ordinary tap water. The method can be utilized to promote healing of animals, by providing a good electrical contact with the epidermis of the animal, which may involve shaving of the contact area to achieve good contact.

The probes are moveable and independently adjustable within each socket, and the source of power is both low voltage and low frequency (low amperage). A user of the invention does not feel the electrical voltage or impulses, as the voltage, wattage, and current are so low as to prevent such sensation.

Low voltage, which is a common term used with many electrical devices today, means that a device operates at twelve volts or less. This can be done by utilizing a transformer to step down the voltage or by utilizing batteries as the source of power.

In an article published in the International Journal of Dermatology, vol. 29, pages 446–450, July–August, 1990, entitled "The Biological Effects of a Pulsed Electrostatic Field with Specific Reference to Hair" the authors discuss the use of low voltage and low amperage in their experiment. It was stated that a dangerous power level corresponds to 300 million volts per meter (v/m) and that a test was performed on mice at a level of 190,000 v/m in a 60 Hertz field for 1,500 hours, over the course of ten and a half months, with no detected adverse health effects. Further it was stated that the human subjects of the experiment were exposed at a level of less than 4,000 v/m for a shorter period of time.

Medical literature contains many references to the use of low voltage, low amperage devices in the treatment of patients. An article published in Osteopathic Medical News, date unknown, pages 34 and 35 describes the use a "Microelectrical Neuromuscular Stimulation" device referred to as (MENS). That device has an amperage current range of 10 $\mu$A to 600 $\mu$A and frequencies ranging from 0.1 Hz to 990 Hz, which are the same as those useful in the present invention. Advantageously, the amperage used with the invented apparatus is 80 $\mu$A at frequencies of 0.3, 0.7, 30 and 50 Hz, all well within the range reported in the above mentioned article.

The article entitled "Electrotherapy for Acceleration of Wound Healing; Low Intensity Direct Current" in Arch Phys Med Rehabil Vol 54, July 1985, describes standardizing a protocol for using the low intensity direct current (LIDC) of 200 $\mu$A to 400 $\mu$A for normally innervated skin and 400 $\mu$A to 800 $\mu$A for denervated or decentralized skin applied at the wound site. The result was healing rates of 2 to 3.5 times faster than those of the control subjects.

An article entitled "EMR . . . The Electronic Answer to Resistant Muscular Problems" (Wing, EMR . . . The Electronic Answer to Resistant Muscular Problems, Digest of Chiropractic Economics, 118–126, November–December (1982)), includes a discussion of treating a patient with between 40 $\mu$A and 600 $\mu$A of current. Again, these values are within the useful range of the present invention.

These articles indicate that the range of current, voltage and waveform are readily determinable by one of ordinary skill in the art.

The invented apparatus is preferably powered by a device which is capable of providing: waveform; polarity; frequency; and current, and is preferably powered by eight (8) D-Cell batteries, of 1.5 volts each. These types of machines are commercially available. With such a control device, the voltage can be regulated in the very low voltage range, i.e., the milliamp, millivolt ranges, and even into microvolt and microamp ranges. Each electrical stimulation treatments should last about 15 minutes, and preferably not more than one to three times per week. Individual settings must be determined in accordance with the health and physiological differences of each user.

SUMMARY OF THE ACHIEVEMENT OF THE OBJECTS OF THE INVENTION

From the foregoing, it is readily apparent that I have invented an improved method and apparatus for promoting healing of both skeletal tissue and soft tissue of a mammal, and for reducing pain, including headache pain. Further, the invented apparatus promotes healing of damaged human tissue without further injury or burning of tissue.

It is to be understood that the foregoing description and specific embodiments are merely illustrative of the best mode of the invention and the principles thereof, and that various modifications and additions may be made to the apparatus by those skilled in the art, without departing from the spirit and scope of this invention, which is therefore understood to be limited only by the scope of the appended claims.

What is claimed is:

1. Apparatus for electrical stimulation of a human scalp, comprising:
   a. an oval shaped hood adapted to fit on a human head to be treated;
   b. said hood being provided with a multiplicity of spaced holes for receiving electrode sockets therein;
   c. electrode sockets situated in at least some of the spaced holes;
   d. probe means associated with and moveable within each socket for adjustably and independently contacting the epidermis of a human head within said hood;
   e. a source of low voltage, low frequency power; and
   f. electrical connections communicating with said power source and each said probe means.

2. Apparatus according to claim 1, wherein each spaced hole has a perimeter defining an edge, each electrode socket is an adaptor provided with at least three generally equally spaced exterior flanges which bear against the edge of the spaced hole in said hood, thus providing a snug fit for the adapter.

3. Apparatus according to claim 1, wherein said electrical connections are printed circuits on said hood.

4. Apparatus according to claim 1, wherein an electrical connection is provided within each said electrode socket in the form of a printed circuit.

5. Apparatus according to claim 1, wherein said electrical connections to alternating sockets communicate with poles of different polarity.

6. Apparatus for electrical stimulation of mammalian tissue, comprising:
   a. a support member adapted to fit about at least a portion of a mammal to be treated:
   b. said support member being provided with a multiplicity of spaced holes for receiving electrode sockets therein;
   c. electrode sockets situated in at least some of the spaced holes;
   d. probe means associated with and moveable within each socket for adjustably and independently contacting the epidermis of a mammal within said support member;
   e. a source of low voltage, low frequency power;
   f. electrical connections communicating with said power source and each said probe means; and
   g. each said electrode socket being provided with a wire situated within each socket for forming a contact with each said probe means and connected to the source of low voltage, low frequency power.

7. Apparatus according to claim 6, wherein said electrical connections to alternating sockets communicate with poles of different polarity.

8. Apparatus according to claim 6, wherein each spaced hole has a perimeter defining an edge, each electrode socket is an adapter provided with at least three generally equally spaced exterior flanges which bear against the edge of the spaced hole in the support member, thus providing a snug fit for the adapter.

9. Apparatus according to claim 6, wherein said electrical connections are printed circuits on said support member.

10. Apparatus according to claim 6, wherein an electrical connection is provided within each said electrode socket in the form of a printed circuit.

11. Apparatus for electrical stimulation of mammalian tissue, comprising:
   a. a support member having an inner surface and an outer surface adapted to fit about at least a portion of a mammal to be treated:
   b. said support member being provided with a multiplicity of spaced holes for receiving electrode sockets therein;
   c. electrode sockets situated in at least some of the spaced holes;
   d. probe means associated with and moveable within each socket for adjustably and independently contacting the epidermis of a mammal within said support member;
   e. a source of low voltage, low frequency power; and
   f. electrical connections communicating with said power source and each said probe means;
   g. each said electrode socket being an adapter, generally tubular in form, having a flange at one end thereof for mating against the inner surface of the support member, and being provided with a tapered central elongated hole adapted to receive each said probe means.

12. Apparatus according to claim 11, wherein a portion of the adapter protrudes exteriorly from the outer surface of the support member, said protruding portion of the adapter having at least one elongated slot, whereby a biasing pressure is created against said probe means within the central elongated hole.

13. Apparatus according to claim 11, wherein said electrical connections to alternating sockets communicate with poles of different polarity.

14. Apparatus according to claim 11, wherein each spaced hole has a perimeter defining an edge, each electrode socket is an adapter provided with at least three generally equally spaced exterior flanges which bear against the edge of the spaced hole in the support member, thus providing a snug fit for the adapter.

15. Apparatus according to claim 11, wherein said electrical connections are printed circuits on said support member.

16. Apparatus according to claim 11, wherein an electrical connection is provided within each said electrode socket in the form of a printed circuit.

* * * * *